US009551995B2

(12) United States Patent
Feine et al.

(10) Patent No.: US 9,551,995 B2
(45) Date of Patent: Jan. 24, 2017

(54) TIP-BASED COMPUTER CONTROLLED SYSTEM FOR A HAND-HELD DENTAL DELIVERY DEVICE

(71) Applicant: James Feine, Bellaire, TX (US)

(72) Inventors: James Feine, Bellaire, TX (US); Mohammad Ali Jamnia, Pleasant Prairie, WI (US); William L. Bollig, Elk Grove Village, IL (US)

( * ) Notice: Subject to any disclaimer, the term of this patent is extended or adjusted under 35 U.S.C. 154(b) by 0 days.

(21) Appl. No.: 14/203,465

(22) Filed: Mar. 10, 2014

(65) Prior Publication Data

US 2016/0299510 A1 Oct. 13, 2016

Related U.S. Application Data

(63) Continuation of application No. 13/517,652, filed on Jun. 14, 2012, now Pat. No. 8,670,858, which is a continuation of application No. 12/513,850, filed as application No. PCT/US2007/084953 on Nov. 16, 2007, now Pat. No. 8,204,612.

(60) Provisional application No. 60/866,201, filed on Nov. 16, 2006, provisional application No. 60/866,231, filed on Nov. 17, 2006.

(51) Int. Cl.
| A61C 1/08 | (2006.01) |
| A61C 3/00 | (2006.01) |
| G05B 15/02 | (2006.01) |
| G05D 7/06 | (2006.01) |

(52) U.S. Cl.
CPC ............. *G05D 7/0617* (2013.01); *G05B 15/02* (2013.01)

(58) Field of Classification Search
CPC ......... A61C 1/08; A61C 3/00; A61C 2204/00; G05B 15/02
See application file for complete search history.

(56) References Cited

U.S. PATENT DOCUMENTS

| 7,258,546 B2* | 8/2007 | Beier ................. A61B 17/1626 433/104 |
| 7,758,342 B2* | 7/2010 | Lewallen ............. A61C 19/041 433/215 |
| 8,758,011 B2* | 6/2014 | Regere ................ A61C 1/0015 433/119 |
| 2003/0205858 A1* | 11/2003 | Hall ........................ F16F 1/025 267/154 |
| 2004/0209223 A1* | 10/2004 | Beier ................. A61B 17/1626 433/99 |
| 2004/0255409 A1* | 12/2004 | Hilscher ................ A61C 17/22 15/22.1 |

(Continued)

*Primary Examiner* — Ronald Hartman, Jr.
(74) *Attorney, Agent, or Firm* — Daniel N. Lundeen; Lundeen & Lundeen PLLC

(57) ABSTRACT

A tip-based computer controlled system for a dental delivery device is disclosed. The system automatically controls an operating characteristic such as power control or fluid flow based on tip identification and history. The operating characteristic may also be controlled in response to particular conditions throughout the dental procedure, such as (but not limited to) temperature, dental hygiene material, fluid type, etc. The system may provide an alert or shut off if unsafe conditions occur and/or error circumstances are detected. An operator interface is provided to configure the system and augment/override an executing control algorithm during a procedure. A method and a computer-readable storage medium are also disclosed.

5 Claims, 7 Drawing Sheets

(56) References Cited

U.S. PATENT DOCUMENTS

| | | | |
|---|---|---|---|
| 2007/0094822 A1* | 5/2007 | Gatzemeyer | A46B 15/0002 15/105 |
| 2007/0190485 A1* | 8/2007 | Hayman | A61C 1/07 433/118 |
| 2008/0221564 A1* | 9/2008 | Rouiller | A61C 3/00 606/40 |
| 2008/0293008 A1* | 11/2008 | Regere | A61C 1/0015 433/119 |
| 2011/0122987 A1* | 5/2011 | Neyer | A46B 15/0002 377/15 |

* cited by examiner

TIP-BASED COMPUTER CONTROLLED SYSTEM FOR A HAND-HELD DENTAL DELIVERY DEVICE

CROSS REFERENCE TO RELATED APPLICATIONS

This application claims priority as a continuation application of U.S. patent application Ser. No. 12/513,850 filed Oct. 15, 2009, now U.S. Pat. No. 8,204,612, which is the United States National Stage under 35 U.S.C. §371, of International Application No. PCT/US2007/084953, having an international filing date of Nov. 16, 2007 and claiming priority to U.S. Provisional Application No. 60/866,201, filed Nov. 16, 2006 and U.S. Provisional Application No. 60/866,231, filed Nov. 17, 2006 the teachings and disclosures of which are hereby incorporated in their entireties by reference.

BACKGROUND OF THE DISCLOSURE

1. Field of the Disclosure

This disclosure relates generally to the automatic control of hand-held dental instruments based on tip identification and controlling corresponding operating characteristics such as power control and fluid flow rate in response to particular conditions.

2. Background Description

An operator may use a powered hand-held instrument to deliver dental services to a patient. This hand-held dental delivery device may be powered by electricity or some other energy source. Examples of such dental devices include ultrasonic scalers, power polishers, and instruments for providing abrasion.

Hand-held dental delivery devices have evolved over the past decades. New techniques have been developed to expand and utilize the power and functionality of dental services, thus necessitating development of new generator circuitry, new insertable tip types and shapes, and new frequencies. This evolution has led to more complexity for operators. In addition to the functional knowledge of each different tip type, an operator must also be knowledgeable about controlling operating characteristics for each different tip during a dental procedure to create optimum procedural conditions and provide a safe environment. Examples of these operating characteristics include the energy or power level delivered to the device and the rate of fluid flow to the hand-held dental device.

Typically, an operator may control the power delivered to these hand-held devices by using an operator control input mechanism such as a switch, button, or foot pedal. The operator is enabled, via an operator control input mechanism, to adjust the power level during a dental procedure. For example, while using an ultrasonic scaler tip, a stubborn piece of tartar may require the operator to increase the power to the device in order to successfully remove it. Or, a more sensitive tooth area may warrant the operator to decrease the power delivered to a polisher.

A safe energy or power level for each tip must be maintained by the operator. For instance, the optimum safe power range (minimum and maximum energy level sent to the handpiece) of an extremely thin tip is much smaller than the safe power range of a very thick tip. If the handpiece of the dental device is driven at a level to induce maximum movement of the thickest tip type and an extremely thin tip type is placed into the handpiece, the maximum safe power of the extremely thin tip type would be exceeded. The extremely thin tip type may fatigue more rapidly and break. The tip may be rendered useless before its expected lifetime and may create a hazardous situation for the patient and the operator. Some tip types may also result in excessive vibration at unsafe power levels that may cause patient discomfort or make control of the tip difficult for the operator.

In addition to power level control, the operator must also pay attention to proper fluid flow rate for each type of dental delivery device. Fluids such as gas or liquid may be required during powered instrumentation use. For instance, while using a band-held dental device during ultrasonic scaling, water may be used as a coolant to dissipate heat that builds up in the handpiece of the dental delivery device. Liquids may act as a lubricant as well as a spot coolant at the tooth surface. They may also act as a flushing agent to remove debris from the cleaning site or as a medicament delivery system. A gas such as air may be used to dry or to clean a tooth site. Nitrous oxide may be used to provide anaesthetic relief to the patient during a dental procedure.

Fluid delivery through a hand-held powered dental delivery device may be controlled by a solenoid and a manual metering valve or regulator. The solenoid may control the on/off action of the fluid flow, and the metering valve/regulator may control the flow rate. Typically, the solenoid may be controlled by a foot pedal switch, and the flow rate may be manually controlled by a valve mounted on the unit, remotely on the dental cart or chair, or integrated into the handpiece. The operator thus may be required to use his/her hands to make adjustments to fluid delivery in addition to using the dental delivery device during the dental procedure. For instance, if a dental device requires more power to scale a stubborn piece of tartar, heat may be built up in the dental device and at the tooth site, thus requiring the operator to manually increase the flow of water for cooling. The operator may then use his/her fingers to adjust the valve to decrease the amount of water after the piece of tartar has been removed. In another example, the operator may need to manually increase the flow of a medicament while the hand-held dental device is in proximity to the site of intended application of the medicament, and decrease the flow as the instrument moves away from the site.

The evolution of hand-held dental delivery devices requires increased operator vigilance and attention to different tips, their associated characteristics and the adjustment of corresponding operating characteristics such as power levels and fluid flow rate. This forces the operator to break focus during a dental procedure, thus contributing to operator fatigue. Manual control may be cumbersome. Operator mistakes may result in premature fatigue or breakage of the dental device tip. Potential contamination of the dental site is possible through the operator's hands and fingers since s/he needs to manipulate controls throughout the procedure. A way of automatically controlling operating characteristics to a hand-held dental delivery device based on tip is needed to address these shortcomings.

BRIEF SUMMARY OF THE DISCLOSURE

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

A tip-based computer controlled system for a dental delivery device may address the shortcomings of manual control as discussed in the Background. Such a system may include a powered hand-held dental delivery device. The dental delivery device may include a handpiece able to receive insertable tips for performing various dental tasks such as ultrasonic scalers, powder polishers, abrasion devices, and the like, or a separate integral delivery device may be used for each different task. A computer, microprocessor or device driver may be enabled to automatically determine what type of device and/or device tip is being used.

Such hand-held devices with or without insertable tips, the automatic determination of tip identification and the storage of usage history for each tip are described in U.S. Application No. 60/806,807, filed Jul. 10, 2006. The tip-based computer controlled system of the present disclosure may operate with such dental devices. These dental devices may include a tip identifier system that allows a microprocessor, computer or device driver to determine the tip by distinguishing a unique shank shape corresponding to a unique insertable tip, by using a drive coil as a detection antenna to communicate information, or by reading an RFID, barcode, or the like. Once determined, the identified tip may correspond to an associated stored profile containing characteristics, identification numbers, a history of the tip's usage and other associated static and dynamic data. The stored profile may be co-located with the microprocessor or computer, it may reside in a remote accessible database, or the stored profile may be retained in a memory of the dental delivery device itself. Alternatively, the operator may input the tip, its characteristics, profile and history into the computer. (As used herein, the term "operator" is intended to be interpreted to include a dental professional using the dental delivery device to perform a dental procedure, or a person in an administrative capacity who may program the computer for use by the entire dental office or in preparation for a specific dental procedure.) The device or device tip may also have the ability to receive data from the device driver/microprocessor to store into its non-volatile memory, thus enabling the or device tip to be used in various locations and/or offices and retain its profile and history.

Tips may be integral with the handpiece. Alternatively, they may be an exchangeable tip, head or cartridge inserted into the handpiece of the dental device. If the device is a one-use device, such as a one-use prophy cartridge, the microprocessor/computer would not necessarily need to communicate bi-directionally. One-use devices are disclosed, for example, in U.S. application Ser. No. 11/162,069, filed Aug. 26, 2005. Such a single use device/cartridge may be used in a tip-based computer controlled system.

The tip-based computer controlled system of the present application may include a computer, microprocessor or device driver that uses the stored profile of the device tip to determine, set and store boundary parameters and control algorithms for "operating characteristic" control. An "operating characteristic" of the tip-based computer controlled system as used herein may include any controllable aspect of the dental procedure that may need to be dynamically altered during the execution of the procedure, and hereinafter may be abbreviated as "OC". Examples of such OCs may include power level and fluid flow rate. Typically, an operating characteristic may have a source (such as a power generator or a fluid supply), an operating characteristic (OC) controller in communication with both the dental delivery device and the microprocessor (such as a power control mechanism or a flow valve), a mechanism for operator control input mechanism (such as a foot pedal or switch), and a connection with the hand-held device to deliver the OC to the hand-held device. The OC controller may be co-located with the computer, the OC source or the hand-held device, or it may be a discrete entity.

The computer, microprocessor or device driver may be the same entity as the computer of the tip identification system or it may be a different machine. Likewise, the boundary parameters and control algorithms for OC control may be housed in the same or different entity that maintains the stored tip device profile. With the advances in direct and wireless computer networking, remote and local storage, internet access and different device types, numerous electronic storage, networking and communication configurations and methods are possible and may be used in the system of the present disclosure.

In a tip-based computer controlled system, the operating characteristic may be controlled by the microprocessor in accordance with control algorithms that incorporate the tip device profile and boundary parameters. An initial/default level of operating characteristic may be set by the operating characteristic control algorithm based on the tip device profile. Boundary parameters may include operating zone maximum and minimum levels, levels at which a user notification, alert or alarm is generated and resulting actions to be taken. The OCs, initial/default levels, boundary parameters, control algorithms and their correspondence to specific tips may be pre-selected and pre-determined. Or, they may be loaded into the computer/microprocessor via a disk, a device, a local database, a download from a server, website or other location via any known directly connected or wireless connection standard or by some other transfer means, either a priori or automatically upon determination of the tip identification. The OCs, initial/default levels, boundary parameters, control algorithms and their correspondence to tips may be partially or entirely input to the system and/or modified by an operator after the initial loading. The tip-based computer controlled system may also include an operator override control to enable an operator to override a default level, to move out of an OC's optimum operating zone temporarily during a dental procedure, or to initiate an emergency stop.

Consider the embodiment of using the tip-based computer controlled system for adjusting the operating characteristic of power delivered to a hand-held dental device. This embodiment describes using electric power delivered to the hand-held device, but other embodiments using different types of power sources are also possible. A stored profile, control algorithm(s) and boundary parameters corresponding to a specific tip, head or cartridge may be loaded, downloaded or otherwise entered into the system a priori or automatically upon determination of the tip identification. Alternatively, the stored profile may be obtained from a memory located in the hand-held dental device. Upon determination (via direct operator input or other methods known in the art as discussed above) that the specific tip has been selected by the operator for use in a dental procedure, the system, based upon the corresponding control algorithm, may set an optimum initial power level if the stored profile of the tip so requires. Additionally, the operator may choose to override the initial power level and/or input new or modified desired boundary parameters before the procedure begins. The system may also communicate to the operator any pertinent usage information via the operator interface, such as tip wear, device warnings (e.g., don't use on a patient with a pacemaker), possible medical interactions, and the like.

The operator may begin to use the device in the dental procedure and may apply power to the device via a standard operator control input mechanism such as a hand control or a foot pedal. Deviations to the initial frequency and power level may be indicated by the operator and executed by the system based on the control algorithm(s). While the dental device is in use, the control algorithm(s) may prescribe the computer to take no action if the frequency and the power level being delivered to the dental device remain in the optimum range as prescribed by the power control algorithm. However, if the power level and/or frequency exceeds a first threshold (as defined by a pre-determined or operator-modified boundary parameter), the control algorithm(s) may prescribe the computer to generate an alert to notify the operator and request approval for continuation. If the operator wishes to continue, s/he may indicate this via an operator override control or other input. If the power level and/or frequency exceeds a second threshold, the system may generate a visual or auditory alarm. Multiple different threshold levels and resulting actions may be defined in the system and set as desired. In an emergency situation, such as a power spike, the system may automatically shut off power to the dental device. Alternatively, the operator may initiate an unexpected shut off, such as when a patient indicates discomfort or is gagging.

After the procedure has finished, the tip-based computer controlled system may log the events of the procedure associated with the tip. Examples of logged data may include the power levels used during the procedure, maximum power usage, history of usage, failure to vibrate correctly or other failure conditions, timestamps associated with various events, and the duration of operation at those power levels. Other logged data may be captured. The types of data to be logged for a procedure or a tip may be specified a priori by the operator. The log may be stored with the tip device profile or in another data storage area locally, remotely, on a device, a server a website or other data storage means. The log may be used to provide notification of any routine maintenance requirements, service issues, errors and the like for the tip and/or device. The log enables the data history to be accessed by the office, manufacturer, regulatory agencies or other consumers. The tip profile may also be updated to reflect usage during the procedure.

Tip-based computer controlled systems for a handheld dental device may also be used to automatically control the operating characteristic of fluid flow rate. A dental device may include a fluid conduit within the handpiece for delivering fluid to the dental site. The fluid conduit may be connected to a fluid supply and a fluid generator. Fluids used by the system may be gases or liquids required for various dental procedures such as air, nitrous oxide, water, steriulents, medicaments or other fluid. For example, water may be used to flush debris from a dental cleaning site, to act as a coolant to dissipate heat in the handpiece, or to spot cool the tooth surface. A liquid disinfectant may be delivered to the tooth to sterilize the site. Another example may be the delivery of a numbing medicament during a dental task, or the use of air to dry a tooth surface.

The connection of the fluid supply to the conduit in hand-held device may be mechanically switched between different types of fluid supplies. Alternatively, a unique set of tubing and hoses may be used for each different type of fluid supply. Other fluid connection configurations may be possible.

The tip-based computer controlled system may include a digitally controlled flow valve located between the dental delivery device and the fluid supply. One type of digitally controlled flow valve, for instance, may be the Type 2824 2/2-way Proportional Valve by Burket™. Other types of digitally controlled flow valves may also be used. The digitally controlled flow valve may be housed in a stand-alone unit, it may be housed in the same unit as the hand-held device, or it may be housed in the same unit as the fluid supply. In an exemplary embodiment of the tip-based computer controlled system, the digitally controlled flow valve may operate in conjunction with a microprocessor to regulate the flow of fluid to the handpiece. The microprocessor may be in communication with the hand-held device and the flow valve, and may automatically provide total or a portion of fluid flow rate control so that the operator is freed to concentrate on conducting the dental procedure. The microprocessor may be housed in the same unit as the hand-held device, the digitally controlled flow valve or the fluid supply. Another embodiment may include the microprocessor housed in a separate unit or computer. The microprocessor may be in communication with the hand-held device and the flow valve.

One or more flow control algorithm(s) may set an initial flow rate based on the determined tip, tip profile and fluid type. The flow control algorithm(s) may also prescribe how fluid flow may be varied by the microprocessor corresponding to at least one of several conditions, including, for example, the power level needed to perform the dental task, the temperature of the dental device and/or the dental site, the dental hygiene material used during the dental task, or an input detected by an operator flow control input mechanism. Flow control may also be based on a combination of one or more conditions. The control algorithm(s) may be predetermined and loaded into the microprocessor, one or more portions of the control algorithm may be specified by an operator and then loaded into the microprocessor, or a real-time operator interface may be used to allow the operator to specify one or more boundary parameters and one or more portions of a flow control algorithm before each dental procedure. Additionally, a current flow control algorithm may be augmented or overridden by the operator at any time before or during a procedure through an operator flow control input, for instance, to maintain full manual control, to stop the flow if a patient is gagging or to customize the fluid flow to the operator's liking.

In one embodiment, the microprocessor may determine the type of tip and tip identification being used, for instance, by distinguishing a unique shank shape corresponding to a unique insertable tip, by using a drive coil as a detection antenna to communicate information, or by reading an RFID, barcode or other computer-detectable characteristic. A stored profile, control algorithm(s) and boundary parameters corresponding to a specific tip may be loaded, downloaded or otherwise entered into the system a priori or upon determination of the tip identification. Or, the stored profile may be obtained from a non-volatile memory of the hand-held device or tip. Alternatively, the operator may be able to input tip identification information to the microprocessor. Other ways of determining the tip may be possible and are known in the art. The system may also communicate to the operator any pertinent usage information related to the tip via the operator interface, such as tip wear, device warnings (e.g., don't use on a patient with a pacemaker), possible medical interactions, and the like.

The flow control algorithm may then set a default level of fluid flow based on the information in the tip profile, fluid type and boundary parameters. For instance, an ultrasonic scaler may require a particular flow rate of water to flush debris, while a polisher may require a lesser flow rate of water to mix with the polishing material.

In another embodiment, the microprocessor, according to the control algorithm, may receive an indication of the power being applied to the tip and may automatically increase fluid flow as the power level increases (and correspondingly decrease fluid flow as the power level decreases). An example of this is during ultrasonic scaling—if a stubborn piece of tartar requires more power to the dental delivery device, more heat may build up and require more water for cooling. In one embodiment, an operator may adjust the power level to a dental delivery device via a foot pedal connected to the hand-held device, and the control algorithm for the tip may increase the fluid flow accordingly. The microprocessor may be in electrical connection with the foot pedal and may control the digitally controlled flow valve according to power variation.

Another automatic control of fluid flow may correspond to temperature, either of the tooth site or of the dental device itself. In these cases, a thermocouple or other type of temperature sensor may be positioned at or near the tip of the dental device or within the dental device handle, and detected temperature data may be sent to the microprocessor. As the detected temperature rises, the fluid flow may be adjusted by the microprocessor, based on the control algorithm, to provide adequate cooling to the tooth site and/or dental device.

A dental hygiene material may also be detected by or may be provided to the microprocessor by the operator (i.e., selected from among a plurality of predefined dental hygiene materials listed on a user interface display). The control algorithm may prescribe an automatic adjustment of fluid flow based upon the dental hygiene material to optimize for the specific dental procedure. For instance, if a certain type of polish requires a level of water for use, the microprocessor may set the flow rate to the needed level. As another example, a different flow rate may be required for air abrasion using aluminum oxide.

The tip-based computer controlled system may have a safety feedback loop to detect and respond to error circumstances for safety purposes. For example, consider the scenario where water flow is used to cool the dental device, and for some reason the water supply becomes inaccessible. The temperature sensor may communicate an increasing device temperature to the microprocessor even though the microprocessor has increased the water flow over time. The safety feedback loop may detect this error circumstance and may alert the operator via an audible or visual signal, and/or the system may automatically shut off the dental device. Another example of a safety feedback loop may be the delivery of an anaesthetic. To avoid over-medicating the patient, the safety feedback loop may alert the operator or automatically turn off fluid flow after a predetermined time interval of delivering anaesthetic. Other scenarios requiring safety feedback loops are also possible. The boundaries of the safety feedback loop boundary parameters and the resulting actions (alerts, shutoffs, etc.) may be predetermined or they may be adjustable by the operator.

The operator may also be able to provide input to adjust the flow rate during a dental procedure using an operator flow control input. Some conditions that require flow rate adjustments are detectable only by the operator, for example, the need for a greater amount water to flush a bigger orifice and a lesser amount for a smaller orifice. Other conditions detectable by only the operator may include an increased amount of debris that requires more vigorous flushing, or a patient gagging and requiring cessation of the fluid flow. Additionally, an operator may wish to augment or override the microprocessor's flow control algorithm to adjust the flow for his/her own personal preferences during a procedure. One embodiment of an operator flow control input device mechanism may be a foot pedal. As the operator increases pressure on the foot pedal, the increase in pressure may be detected by the microprocessor and the fluid flow rate may increase, and vice versa. The foot pedal may be the same unit as the operator power control input mechanism or it may be a separate unit. Other embodiments of an operator flow control input mechanism may also be possible, such as a button on the handpiece, a dial on the base unit, and/or an emergency stop switch. The operator may be able to adjust the flow within a designated normal operating range, and if s/he wishes to move outside that range, the safety feedback loop may verify the out-of-range indication with the operator via a user interface.

An exemplary embodiment of fluid flow control may be adjusting the flow of fluid based on a combination of conditions. For instance, increasing power while performing ultrasonic scaling may require a different corresponding flow rate compared to increasing power while performing polishing. Or, delivering one type of liquid coolant to the tooth site may require a different rate than delivering water. The flow control algorithm(s) required for various combinations of conditions may also be predetermined and pre-loaded into the microprocessor, one or more portions of the control algorithm may be specified by an operator and then loaded into the microprocessor, or a real-time operator interface may be used to allow the operator to select boundary parameters and flow control before each dental procedure. Additionally, any real-time adjustments to modify the executing flow control algorithm during a procedure may also be made by the operator via the operator flow control input device.

After the procedure has finished, the tip-based computer controlled system may log the events of the procedure associated with the tip. Examples of logged data may include the fluid flow rates used during the procedure, the duration of operation at those rates, maximum fluid flow, timestamps associated with various events, and usage history. Any unexpected events such as detected increasing temperature in spite of increased fluid flow or other failure events may also be noted for debugging purposes. Other logged data may be captured. The contents and scope of logged data may be pre-determined or may be specified a priori by the operator. The log may be stored with the tip device profile or in another data storage area locally, remotely, on a device, a server, a website or other data storage means. The log may be used to provide notification of any routine maintenance requirements, service issues, errors and the like for the tip and/or device. The log enables the data history to be accessed by the office, manufacturer, regulatory agencies or other consumers. Additionally, the tip profile may also be updated to reflect usage during the procedure.

Note that in some embodiments of the tip-based computer controlled system for a dental hand-held device, interaction between several OCs may be possible. For instance, for a specific tip, if an operator applies more power to the dental device, the site temperature may increase. To mitigate the situation, the microprocessor may increase the flow of fluid delivered to the site to help cool the site, the microprocessor may decrease the power while keeping the fluid flow rate constant, or some combination of the two approaches may be used. Other interactions between different OCs and their respective algorithms may be possible. The control algorithms resulting from interactions and the responses to these interactions by the system may be pre-determined, loaded onto the system via one of the transfer means described above, or input and/or modified by the operator.

DETAILED DESCRIPTION OF THE PREFERRED EMBODIMENTS

Although the following text sets forth a detailed description of numerous different embodiments, it should be understood that the legal scope of the description is defined by the words of the claims set forth at the end of this patent and equivalents. The detailed description is to be construed as exemplary only and does not describe every possible embodiment since describing every possible embodiment would be impractical. Numerous alternative embodiments could be implemented, using either current technology or technology developed after the filing date of this patent, which would still fall within the scope of the claims.

It should also be understood that, unless a term is expressly defined in this patent using the sentence "As used herein, the term '_ _ _ _ _ _' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term by limited, by implication or otherwise, to that single meaning. Finally, unless a claim element is defined by reciting the word "means" and a function without the recital of any structure, it is not intended that the scope of any claim element be interpreted based on the application of 35 U.S.C. §112, sixth paragraph.

Figure 1:
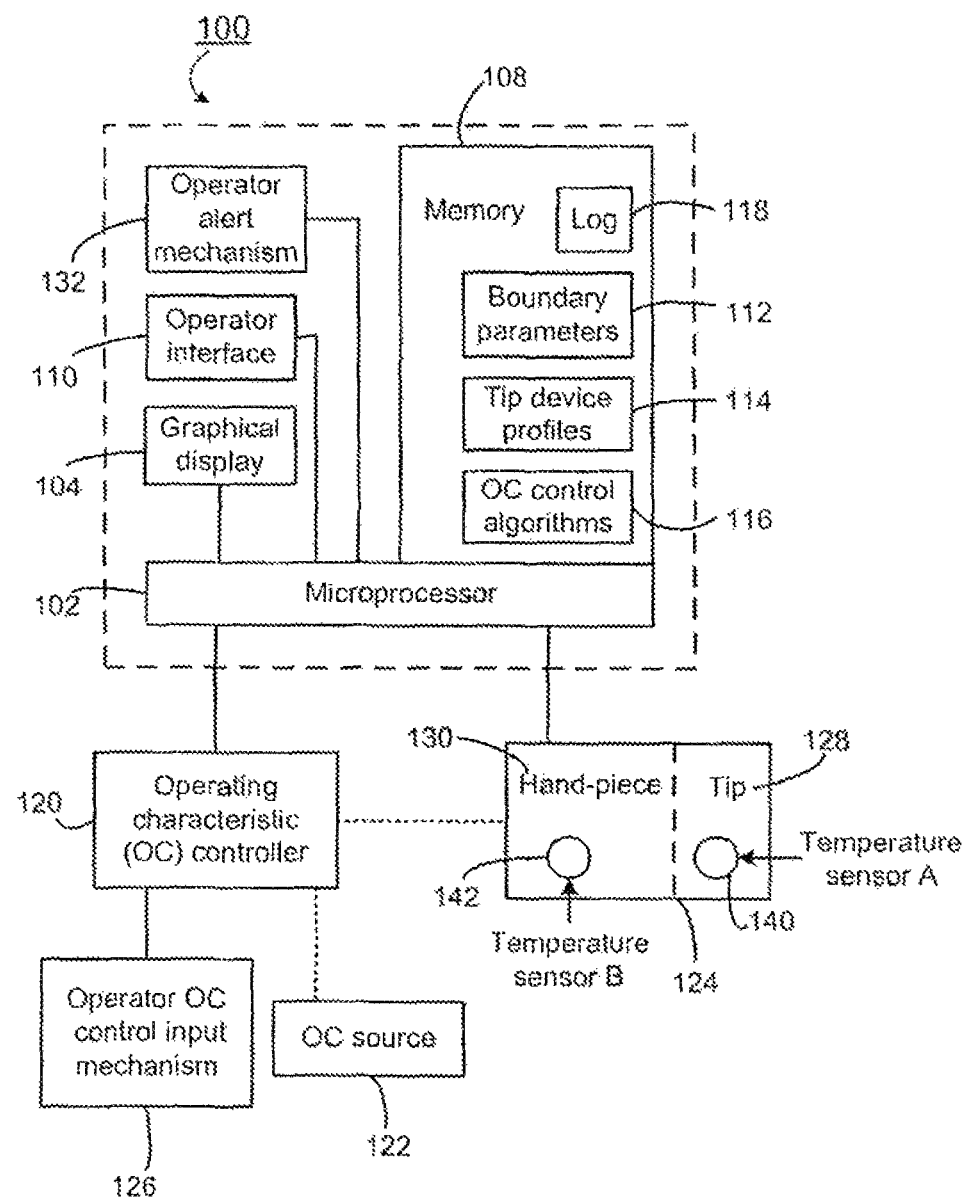
FIG. 1 illustrates an exemplary schematic embodiment of a tip-based computer controlled system for a dental delivery device.

FIG. 1 illustrates an exemplary schematic embodiment of a tip-based computer controlled system 100 for a dental delivery device. The system 100 may include a microprocessor or controller 102 in communication with a graphical display 104, a memory 108, and an operator interface 110. The graphical display 104 may be digital and may include a screen having, for example, a dot matrix display of a liquid crystal display (LCD) type, organic light emitting diode (OLED), or other suitable screen that allows for graphical display of information. The memory 108 may be a random access memory (RAM), a read only memory (ROM), erasable read only memory (EROM), erasable programmable read only memory (EPROM), or other memory typically used in computer devices. The operator interface 110 may be a keyboard, mouse, touch screen, touchpad, or other typical user interface, and may be integrated with the graphical display 104. Also, the operator interface 110 may include a mechanism for a file or data to be loaded into the memory 108, said file or data containing operating boundary parameters 112, tip device profiles 114 and operating characteristic control algorithms 116 for use by the tip-based computer controlled system 100. Examples of loading mechanisms may include a drive, a disk, a download, or other such means that enable the transfer of information into the memory 108 using operator interface 110. The operator interface 110 may also include a mechanism for a file or data to be transferred from the memory 108 to another entity. For example, the log 118 or other output may be able to be transferred to another drive, disk, or computer, or the output may be able to be uploaded to a website or remote server.

Although the boundary parameters 112, tip device profiles 114, OC control algorithms 116 and log 118 are illustrated in FIG. 1 as residing in the memory 108 of the computer, this represents an exemplary embodiment. Another embodiment may include the tip device profile 114 being stored in non-volatile memory of the dental device 124 or the tip itself 128. Other possible embodiments may include one or more of these data entities or portion(s) thereof being stored remotely, on a website, on a different computer or server, on a device, or other storage area. The tip-based computer controlled system for a hand-held dental device 100 may take the form of any embodiment where the microprocessor 102 is able to access these data entities 112, 114, 116, and 118.

After the initial transfer into memory 108, the operator may use the operator interface 108 to modify the boundary parameters 112, tip device profiles 114 and OC control algorithms 116. As previously defined in the Summary, an "operating characteristic" (CC) may be any aspect of the dental procedure that may need to be dynamically altered during the execution of the procedure. Examples of OCs may include power level and fluid flow rate. The OC control algorithms 116 may define an initial/default level and how the operating characteristic levels may be automatically altered during the use of a tip. The memory 108 may also contain a log 118 that may be (but not necessarily) associated with the tip device profiles 114.

A tip device profile 114 may contain identification for the tip such as manufacturer, serial numbers, date of manufacture and the like. It may also contain characteristics of the tip such as intended usage, shank size, material composition, etc. A usage history (not pictured) may also be associated with the tip device profile 114 containing information such as the date and duration of usage with a certain handpiece in a certain office, etc. Other static and dynamic data may be included in the tip device profile 114.

The tip-based computer controlled system 100 may have an OC controller 120 in electrical communication with the microprocessor 102. The electrical communication may be a direct, networked or wireless connection, or some other type of communication channel known in the art. The OC controller 120 may be operable to receive from the microprocessor 102 instructions for setting a desired operating characteristic level corresponding to the boundary parameters 112, tip device profile 114 and OC control algorithms 116.

The OC controller 120 may control operating characteristic delivery from its source 122 to the hand-held device 124, and it may also be responsive to an operator OC control input mechanism 126. The OC controller 120 may be co-located in the same entity with one or more of the microprocessor 102, the OC source 122, the hand-held device 124 or the operator OC control input mechanism 126, or it may be contained in its own entity.

It will be appreciated by one skilled in the art that there is not necessarily a one-to-one correspondence between a single tip-based computer controlled system 100 and a single OC controller 120 nor is there necessarily a one-to-one correspondence between a single system 100 and a dental device 124. For example, one computer system 100 may service all of the OC controllers 120 in an office or in several offices. Or, in the example of a tip device manufacturer desiring data during the beta-testing a new type of tip, the manufacturer may house its computer system 100 on a website server and allow access from all beta-testing office sites. The log 118 may reside on a website server and the OC control algorithms may be downloaded from yet another website while the boundary parameters 112 and tip device profiles 114 are local to each office. With the advances in direct and wireless computer networking, remote and local storage, internet access and different device types, numerous electronic storage, networking and communication configurations and methods are possible and may be used in the system of the present disclosure.

In one embodiment, the operating characteristic may be electrical power. A specific tip 128 that responds to electric power variations (e.g., ultrasonic scaler, polisher, etc.) may have its tip device profile 114 stored in memory 108. The tip 128 may be inserted into handpiece 130 of hand-held dental device 124, and have the form of an insertable tip, head, cartridge, or the like. Alternatively, the tip 128 may be integral with the handpiece 130. The device 124 may receive its power from a power source 122, and the power controller 120 may control the amount of power delivered from the power source 122 to the hand-held device 124. The power controller 120 may be responsive to an operator power control input mechanism 126, such as a foot pedal, lever, or dial. If the operator increases pressure on the foot pedal, the power controller 120 may respond by delivering/allowing an increase of power from the source of electricity 122 to the hand-held device 124, and vice versa for a decrease of pressure.

Boundary parameters 112, tip device profiles 114 and power control algorithms 116 may define the initial/default power level, an optimum operating range and different alarm thresholds corresponding to tip 128. They may be loaded or may be input by the operator via the operator interface 110 during the initial configuration of system 100. Alternatively, a specific set of boundary parameters 112, tip device profiles 114 and power control algorithms 116 corresponding to an individual tip 128 may be automatically or manually retrieved and loaded after the tip 128 has been selected and identified for the procedure. Control algorithms 116 may vary according to the tip device profile 114 and boundary parameters 112. For example, a control algorithm 116 may specify as a tip 128 ages (as recorded in its profile 114), a maximum power level boundary parameter 112 may be set to a lesser level in order to prevent failure of the tip. In another example, the control algorithm 116 may specify that a maximum power level for a thick tip may be greater than that of a thinner tip. In yet another example, an optimum operating range for a newer tip may be set to be greater/wider than that for an older tip. Other examples of boundary parameters 112 and control algorithms 116 are also possible.

The operator may have the ability to modify boundary parameters 112 and power control algorithms 116 or some subset thereof via the operator interface 100 if so desired.

Various thresholds and their resulting actions may be included in the boundary parameters 112 and power control algorithms 116 for tip 128. They also may be loaded or input by the operator into the system 100. For instance, if the operator exceeds a defined optimum maximum operating power, an alert may be generated via operator alert mechanism 132. The alert may be auditory, such as a tone, series of beeps, or recorded voice. This alert may be a visual alert, for instance, a blinking light or a pop-up window on the graphical display 104. In some embodiments, the operator alert mechanism 132 and the operator interface 110 and/or the graphical display 104 may be the same entity. The alert may inform the operator that a threshold has been reached, and may also request an indication of approval from the operator to continue. In response to the alert, the operator may indicate a desire to override the stored boundary parameters 112 via the operator interface 110, or the operator may choose to decrease power via the operator power control input mechanism 126. The system 100 may respond accordingly to the operator indication.

Other thresholds may also be set for different levels of safety. For instance, in the event of a detected power spike, the system 100 may automatically stop power to the hand-held device 124. Some thresholds may be defined so that they may not be overridden by the operator.

At various points during the procedure or after use of the tip 128 has completed, the log 118 may be updated with data corresponding to the tip 128 usage. This data may include the date, timestamps, handpiece identification, power levels used, durations at various power levels, alarms generated, error circumstances and the like. The types of information recorded in log 118 may be pre-determined or defined by the operator. The log 118 may be associated with the tip device profile 114 or it may be a separate entity. The log 118 may be used to provide notification of any routine maintenance requirements, service issues errors and the like for the tip 128, handpiece 130 and/or device 124. The tip device profile 114 may also be updated to reflect usage of the tip 128.

Another embodiment of the tip-based computer controlled system may have fluid flow as the operating characteristic. In this embodiment, the OC controller 120 may be a digitally controlled flow valve 120. One example of a digitally controlled flow valve 120 may be the Type 2824 2/2-way Proportional Valve by Burket™, but other types of digitally controlled flow valves may also be used in system 100. The flow valve 120 may be in fluid connection with a fluid source or supply 122 associated with a fluid generator (not pictured). The fluid contained by the fluid supply 122 may be water, air, a gas, a steriulent, a medicament, or any other fluid required for use in dental procedures. The flow valve 120 may be in fluid connection with one or more fluid supplies 120 simultaneously and may be mechanically switched between the supplies. Alternatively, a separate flow valve 120 and hose connection may be connected for each different type of fluid supply 122.

The digitally controlled flow valve 120 may also be in fluid connection with a band-held dental delivery device 124. Examples of such devices 124 include ultrasonic scalers, polishers, instruments for abrasion, and the like. The hand-held dental delivery device 124 may have a handpiece 130 connected to the flow valve 120 via a fluid conduit that enables delivery of fluid through the dental delivery device 124 to the dental site. The dental delivery device 124 may also be in electrical connection with the microprocessor 102, where the electrical communication may be a direct, networked or wireless connection, or some other type of communication channel known in the art. Additionally, the device 124 may also have a tip 128 that may be insertable into the handpiece 130 and may be identifiable by the microprocessor 102. Insertable tips for hand-held dental devices and their identification are known in the art. Some examples of insertable tips include ultrasonic tips, air polishing heads, air polishing cartridges and air abrasion cartridges. The tips may be identified by the microprocessor 102 via detection of differently shaped-shanks or other distinguishing physical characteristics, by RFID or transmission over other types of directly connected or wireless data systems, by barcode readers or by other tip identification systems.

The microprocessor 102 may have a flow rate control algorithm 116 stored in its memory 108 that determines an initial fluid flow rate corresponding to the tip device profile 114, as well as appropriate varying levels of fluid flow rates throughout a procedure based on fluid flow boundary parameters 112 and one or more conditions. Based on these factors and detected combinations of conditions, the flow rate control algorithm 116 of the microprocessor 102 may direct the digitally controlled flow valve 120 to adjust the flow rate of the fluid to the dental device 124. The flow rate control algorithms 116 may be predetermined and loaded into the microprocessor 102, or one or more portions of the flow rate control algorithm 116 may be configured via the operator interface 110. The operator configurations may be set during initial integration of the tip-based computer controlled system 100 into the dental office, for example, setting a range fluid flow boundary parameters 112 based on the types of instruments available for use in the office. Additionally, the operator configurations may also be modified and/or defined via operator interface 110 before a specific dental procedure, for example, setting a lower maximum fluid flow rate for a patient who has particularly sensitive gums.

Another embodiment may include an operator fluid flow control input mechanism 126 for the operator to modify a configured flow rate control algorithm 116 during a dental procedure, for instance, if a patient is gagging or if there is a large amount of debris to be flushed. The operator fluid flow control input mechanism 126 may allow the operator to augment and/or override the executing flow rate control algorithm 116 during a dental procedure. The operator fluid flow control input mechanism 126 may be incorporated into the operator interface 110, it may be a separate mechanism such as a dial, gauge, foot pedal, or the like in electrical communication with the microprocessor 102, or it may be a combination of mechanisms. For instance, the operator may increase the flow of fluid by pressing a foot pedal, but may also have an emergency stop button to cease all fluid flow.

The operator fluid flow control input mechanism 126 may use the same operator input as a power control mechanism (not pictured) of the hand-held dental delivery device 124. A power control mechanism enables the operator to control the power delivered to the device 124 during a dental procedure and may typically be a foot pedal, where, for instance, the power supplied to the tip 128 may increase when the operator applies more pressure to the pedal. Other operator device power control mechanisms may also be possible and are known in the art. The operator flow control input mechanism 126 may operate in conjunction with the power control mechanism, so that as the operator increases power to the hand-held device 124, the fluid flow rate may increase as well.

Figure 2:
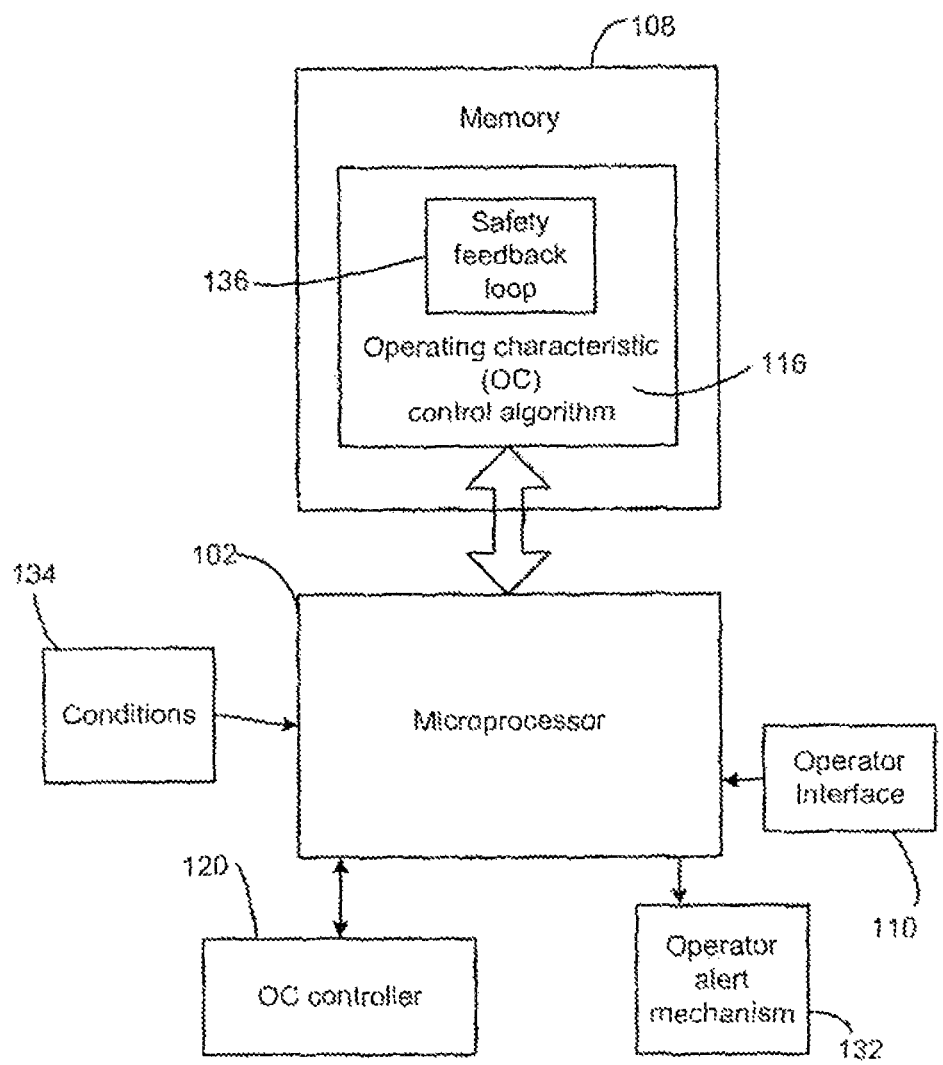
FIG. 2 is a schematic that provides additional detail to the schematic of FIG. 1 by illustrating how inputs are directed to the operating characteristic control algorithm.

FIG. 2 illustrates an embodiment of how detected inputs may be fed through the microprocessor 102 to the flow rate control algorithm 116 resident in the memory 108 of the tip-based computer controlled system 100. As in FIG. 1, an operator may partially or wholly configure the flow rate control algorithm 116 via an operator interface 110 before a dental procedure, or augment and/or override the flow rate control algorithm 116 during a procedure by using an operator flow control input mechanism 126 of FIG. 1 to affect the flow valve 120. Other conditions 134 (that are described below) may also be detected by or received at the microprocessor 102 and may influence the flow rate control algorithm 116. These inputs 110, 120 and 134 may be received at the microprocessor 102 and passed into the flow rate control algorithm 116. The flow rate control algorithm 116 may use these inputs 110, 120 and 134 along with the boundary parameters 112 and tip device profile 114 to determine the appropriate flow rate. Upon determination of the appropriate flow rate level, the microprocessor 102 may then direct the digitally controlled flow valve 120 to modify the flow rate accordingly.

The flow rate control algorithm 116 may include a safety feedback loop 136 for detecting and responding to error circumstances. For instance, the safety feedback loop 136 may detect that in spite of repeated fluid flow increases to mitigate a rising temperature detected at the handpiece 130, the temperature continues to increase. After a predetermined temperature threshold is reached, the safety feedback loop 136 may take mitigating action. For example, it may direct the flow valve (operating characteristic controller of this embodiment) 120 to shut off the fluid flow, it may shut off the device 124 or other parts of the system 100, and/or it may alert the operator via an operator alert mechanism 132 such as a sound or visual indicator. Other examples of scenarios where the safety feedback loop 136 may take action may include but are not limited to timing how long a specific type of anaesthetic has been delivered, or receiving an indication the operator flow control input mechanism 126 through the flow valve 120 that is not commensurate with the type of tip 128 known by the microprocessor 102.

The operator alert mechanism 132 may be incorporated into the operator interface 110, such as a pop-up screen icon or generated sound. It may, via the graphical display 104, request if the operator to verify that s/he wants to continue. Or, the operator alert mechanism 132 may be a separate mechanism from the operator interface 100 and/or the graphical display 104. The operator alert mechanism 132 may be able to be selected and/or configured via the operator interface 110. Additionally, the thresholds and boundary parameters after which the control loop 136 may be triggered into action may be predetermined or some portion may be configured by the operator via the operator interface 110.

Figure 3:
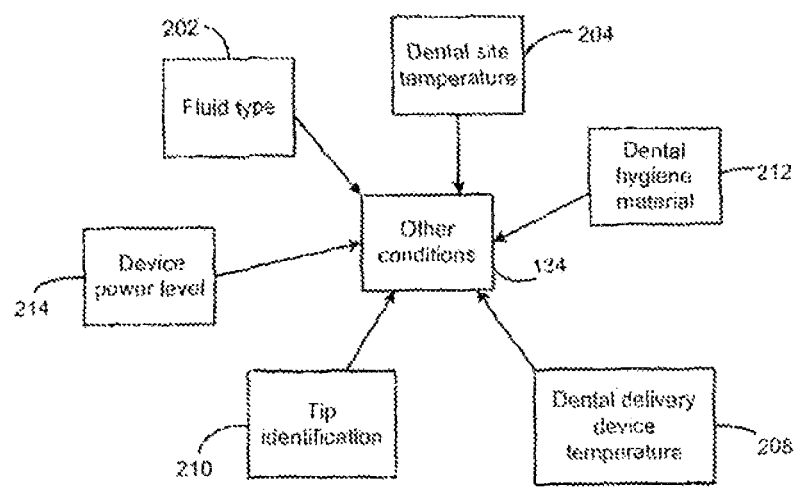
FIG. 3 illustrates an exemplary set of conditions that may affect operating characteristic control.

FIG. 3 illustrates an exemplary set of conditions 134 received at the microprocessor 102 that may be inputs to the flow rate control algorithm 116. The fluid type 202 may be manually input via the operator interface 110 or it may be indicated by the operating characteristic controller 120 (in this embodiment, a digitally controlled flow valve), for instance, when different type of flow valves 120 are used for different types of fluids. The dental site temperature 204 may be detected by a thermocouple or temperature sensor such as temperature sensor A (FIG. 1, reference 140) located in dental device 124 near the tip 128. Temperature readings detected by sensor A (reference 140) may be returned to the microprocessor 102. Likewise, the dental delivery device temperature 208 may be detected by a thermocouple or temperature sensor such as temperature sensor B (FIG. 1, reference 142) located in the handpiece 130 of dental device 124. Temperature readings detected by sensor B (reference 142) may also be returned to microprocessor 102. As discussed earlier, the tip identification 210 may be determined by microprocessor 102 based on a physical characteristic such as shank shape or notification via RFID, barcode, or some other such identification method. Alternatively, the tip identification 210 may be received via operator input at the operator interface 110. Dental hygiene material 212 may also be indicated to the microprocessor 102 via operator input at the operator interface 110. Device power level 214 affecting fluid flow may be indicated via the operator power control input mechanism 126.

Referring to FIGS. 1, 2 and 3, one embodiment of the flow rate control algorithm 116 may categorize conditions 134 into static and dynamic conditions. Static conditions may be those conditions 134 that do not change throughout the duration of a dental procedure, such as tip identification 210, fluid type 202, and dental hygiene material 212. The set of static conditions may be predetermined or may be configurable by the operator. For a static condition or combination of static conditions, an default fluid flow rate and a normal operating range of flow rates may be prescribed by the flow control algorithm 116, either by predetermination, by input of the operator 110, or by some combination of both. During execution, the system, based on the flow control algorithm 116, may set the flow rate at the default level and may allow the operator to adjust the flow rate within the normal operating range boundaries 112. Any flow rate outside of the normal operating range 112 may be detected by the safety feedback loop 136 and may be considered an error condition. Mitigating actions may then be taken. These actions may be configurable and may include alerting the operator 132, asking the operator if s/he wants to continue, shutting off the device, shutting off the fluid flow, or other actions as discussed in previous sections.

Dynamic conditions may be those conditions 134 that may change during a dental procedure such as dental site temperature 204, dental delivery device temperature 208, and device power level 214. The set of dynamic conditions may be predetermined or configurable by the operator. For a given dynamic condition, a dynamic control algorithm 116 and operating boundary parameters 112 may be assigned either by predetermination, by input of the operator 110, or by some combination of both. For example, in the case of the dental delivery device temperature condition 208, the dynamic control algorithm 116 may specify that fluid flow may begin at a given flow rate when a device temperature threshold is reached. The flow rate may adjust according to a predefined set of instructions prescribed by the flow control algorithm 116, e.g., increasing the flow rate by a set amount for each defined increment of detected temperature increase. If a boundary parameter 112, e.g., a maximum temperature for the dental delivery device, is reached, the safety feedback loop 136 may detect the boundary parameter 112 being reached and take mitigating action(s), as previously discussed. Different dynamic conditions may have their individualized corresponding dynamic control algorithms 116 and operating boundary parameters 112.

If multiple conditions 134—either static, dynamic, or a combination of both—occur simultaneously, the flow control algorithm 116 may include a prioritization of conditions 134. Different ranges, boundaries 112, and control algorithms 116 may be used for different combinations of conditions 134, or one condition may take full precedence over another. The prioritization and precedence rules may be predetermined or one or more portions may be input by the operator 110. In all cases, however, the operator flow control input 126 may take precedence over the executing flow rate control algorithm 116, such as in the case of an emergency stop.

Figure 4:
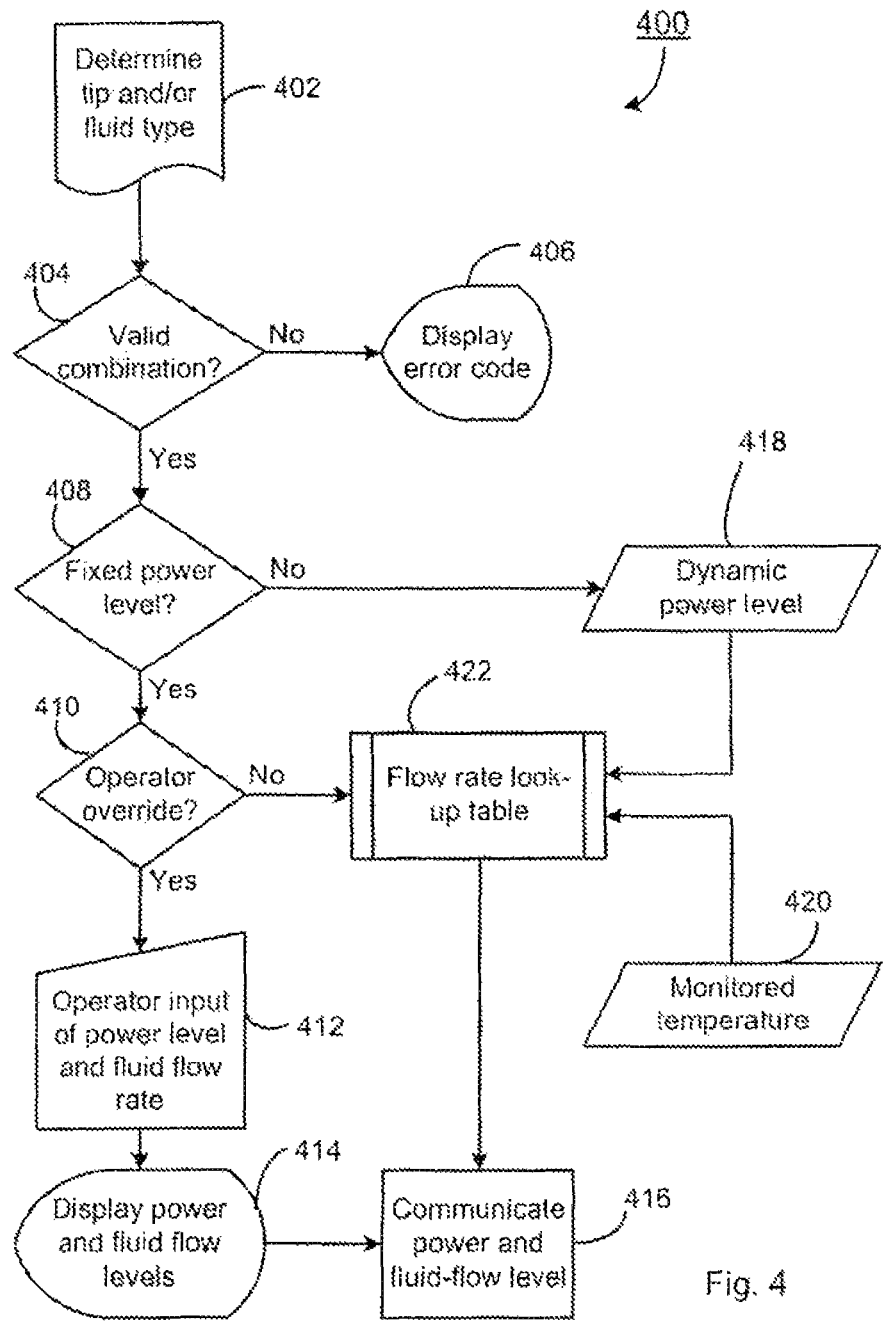
FIG. 4 shows an exemplary embodiment of an operating characteristic control algorithm.

FIG. 4 illustrates an embodiment 400 of an operating characteristic control algorithm such as reference 116 in FIGS. 1 and 2. In this embodiment 400, the operating characteristic may be a fluid flow rate that is controlled via instructions sent to a digitally-controlled fluid flow valve, such as reference 120 in FIGS. 1 and 2. This embodiment 400 of an operating characteristic control algorithm 400 illustrates how operator input, static and dynamic conditions may interact to determine a flow rate within a normal operating range.

Initially at step 402, the tip and/or the fluid type to be used with the tip may be determined or identified, using any of the techniques described earlier. If the combination of tip and fluid type is invalid as determined at step 404, then an error code may be displayed 406 at a graphical display. For instance, if a ultrasonic scaler tip is determined to be used with an anaesthetic fluid type, an error code may be displayed 406.

If the tip and fluid type combination is determined to be valid, a determination may be made at step 408 of whether the power level is desired to be fixed throughout the procedure. If a fixed power level is desired, and an operator override of default system parameters is desired as determined by step 410, then an operator input of the fixed power level and fluid flow rate may be received at step 412. The received fixed power level and fluid flow rate may be displayed 414 at the graphical display and communicated 416 to the fluid flow valve.

Returning to step 408, if a fixed power level is not desired, an indication of dynamic power level may be received, as in step 418. The dynamic power level may be indicated 418, for example, by a foot pedal or switch controlled by the operator. The indication of dynamic power level 418, combined with an indication of a monitored temperature 420 at the dental site and/or at the handpiece, may be used as inputs into a flow rate look-up table 422. Alternatively, a fixed power level as determined via blocks 408 and 410 may be used as the power level input into the flow rate look-up table 422. The flow rate look-up table 422 may be employed if an operator does not want to override the system controls, as determined at step 410. The flow-rate look-up table 422 may determine a fluid flow rate, display it on the user interface 414 and communicate it 416 to the fluid flow valve. Throughout the duration of the dental procedure, updated indications of dynamic power level 418 and monitored temperature 420 may be continually received, resulting in the flow rate look-up table 422 continually updating the graphical display 414 and communicating updated flow rates 416 to the fluid flow valve.

One embodiment of the flow rate look-up table 422 may follow an equation such as:

$$V=h(\text{fluid\_type},g(\text{tip\_id},f(T,P))$$

where V is the determined flow rate, T is temperature, P is power level, and h, g, and f are mathematical terms indicating that V is a function of temperature and power level, a function of the tip identification, and a function of fluid type. This relationship may define a mathematical surface having five dimensions, however, the surface may not be mathematically continuous. Specifically, the surface may shift abruptly as any of the input conditions (temperature, tip_id, fluid_type, power, etc.) change.

As an illustration, consider a scenario where a given fluid type is water, a determined insertable tip identification is model P10 by Hu-Friedy™, and the flow rate is governed by the following relationship:

$$V_1 = a_1 T + b_1 P + c_1 T^* P$$

This relationship may be contained in the flow rate look-up table 422 and employed during a dental procedure using water and insertable tip P10.

In a second scenario, if the given fluid remains the same but the tip is changed from model P10 to model P100 by Hu-Friedy™, a slightly different relationship:

$$V_2 = a_2 T + b_2 P + c_2 T^* P$$

This second relationship may also be contained in the flow rate look-up table 422 and employed during a procedure using water and insertable tip P100. In yet another scenario, the fluid may be some other fluid than water, but the tip identification remains P10, as used in the first scenario. A completely different form of this relationship may determine the resulting flow rate, and be contained in the flow rate look-up table 422:

$$V_3 = a_3 T + b_3 P + c_3 T^* P + x_3 T^2 + y_3 P^2 + z_3 T^{2*} P^2$$

Figure 5:
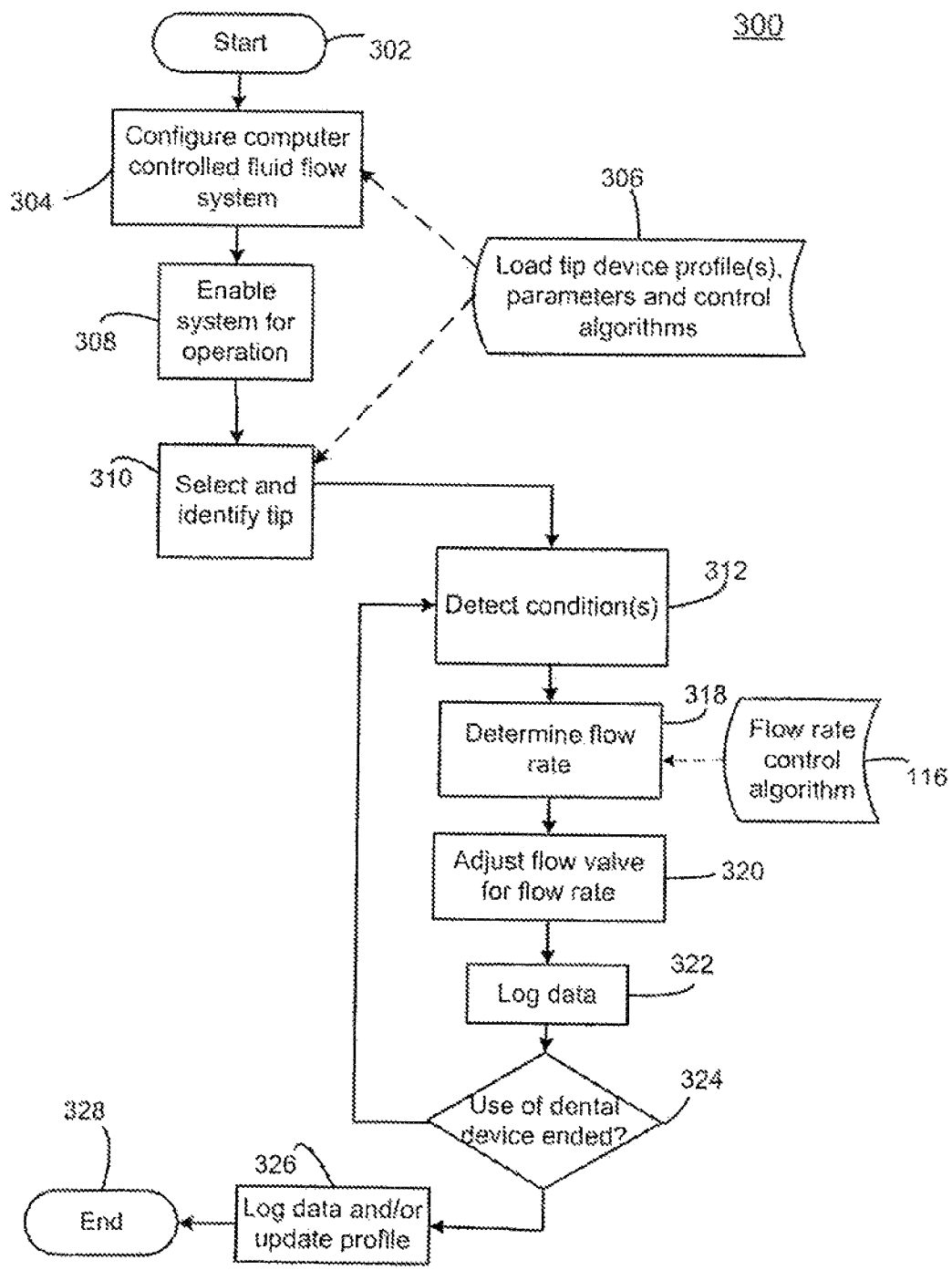
FIG. 5 shows an exemplary embodiment of a method of using a tip-based computer controlled system for a dental delivery device to adjust a fluid flow operating characteristic.

FIG. 5 shows (schematically) an exemplary embodiment of a method 300 using a tip-based computer controlled system 100 for a dental delivery device 124 to adjust the operating characteristic of fluid flow. While the method 300 illustrates steps used for fluid flow, one skilled in the art will appreciate that method 300 is not limited to only an OC of fluid flow, but is easily extensible to other types of operating characteristics such as power delivery and the like.

At the start 302 of the method, the system 100 may be configured, illustrated schematically at step 304. Step 304 may include configuring mechanical connections of the elements in the system 100, such as fluidly connecting the digitally controlled flow valve 120 to the fluid supply/source 122 and to the dental delivery device 124. Step 304 may also include electrically connecting the microprocessor 102 to the dental delivery device 124 and to the digitally controlled flow valve 120, connecting the operator flow control input mechanism 126, establishing network connections if needed, plugging in keyboards and/or other embodiments of the operator interface 110, etc.

Step 304 may also include loading in a set of tip device profiles 114, boundary parameters 112 and flow control algorithms 116 into memory 108 via the operator interface 110, as shown by block 306. The loading 306 may be performed through any possible data transfer mechanism as described earlier in the Summary such as downloading, transferring from another device, etc., or the operator may input or make modifications to the data 112, 114 and 116 via the operator interface 110. In one embodiment of the method, the loading 306 may be performed during system configuration 304. In another embodiment, the complete set of tip device profiles 114, boundary parameters 112 and flow control algorithms 116 may not need to be loaded during system configuration 304, but may be individually retrieved and loaded when a specific tip 128 is selected for use (step 310). Yet another embodiment may load or obtain one or more portions of the different data 112, 114 and 116 from different sources at different times. Examples of data 112, 114 and 116 may include threshold boundary parameters for the safety feedback loop 136, operator alert 132 selection, the range of possible dental device tips 128 and possible fluid types 202, the range of possible selectable dental hygiene materials 212, information required to be logged, and the like.

After the system 100 has been configured in step 304, the system 100 may be enabled for operation 308 and a tip 128 may be inserted into the handpiece 130 of a dental device 124. Alternatively, a dental device 124 without insertable tips may be selected by the operator. The identification of the selected tip 128 is determined 310, and if not done so already during system configuration 304, the corresponding tip device profile 114, boundary parameters 112 and flow control algorithm 116 may be loaded 306. An initial/default flow rate may be set by the flow control algorithm 116. Throughout the usage of the tip 128 during the dental procedure, various conditions 134 as depicted by FIG. 3 may be detected 312, and the data associated with these conditions 134 may be used by the flow rate control algorithm 116 to determine an appropriate flow rate 318. The flow valve 120 may then be directed 320 to adjust to the appropriate flow rate. Any data requiring logging may be recorded 322. (Alternatively, the data may be recorded at the completion of the procedure as in step 326, or at both steps 322 and 326.) If the dental delivery device 124 is still in use as determined by block 324, additional conditions 134 may be detected 312, and the resulting flow rate may be determined 318 and implemented 320. After the use of the tip 128 has ended as determined by block 324, any remaining requested data may be logged 326, and the method 300 may end 328.

Figure 6:
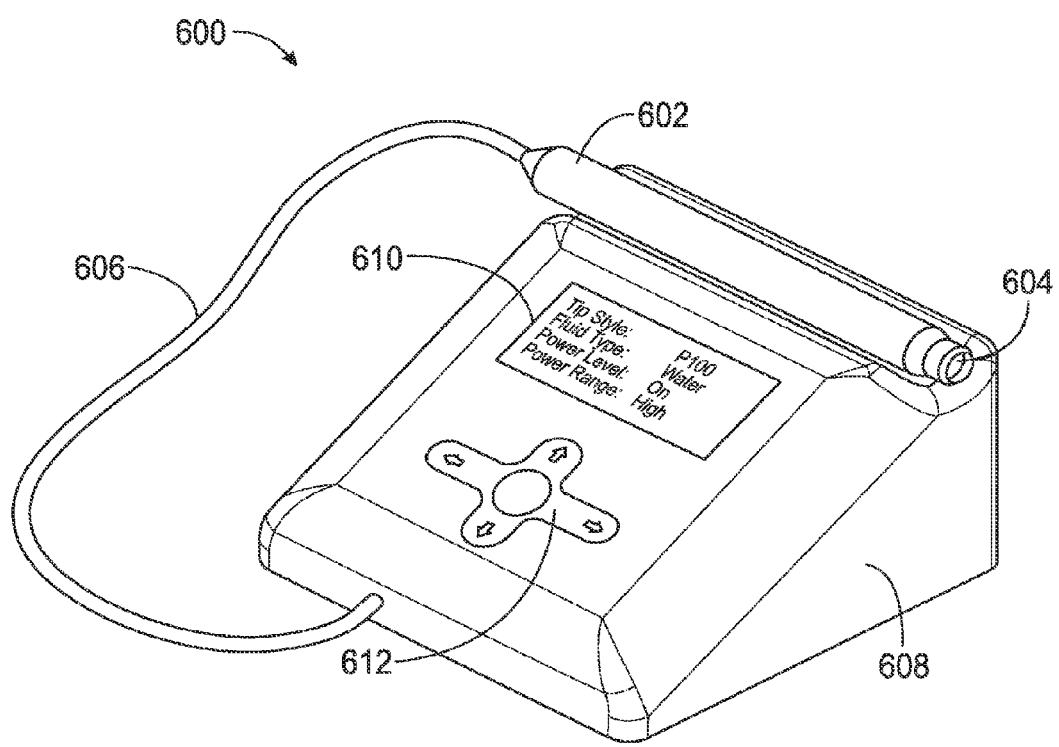
FIG. 6 illustrates an embodiment of a device in a tip-based computer controlled system.

FIG. 6 illustrates an embodiment of a device 600 in a tip-based computer controlled system. In this embodiment 600, the handpiece 602 may have an orifice 604 for receiving an insertable tip (not shown). The handpiece 602 may be in connection 606 with a base unit 608 that may house a microprocessor and a memory (not shown). In this embodiment, the microprocessor may contain the operating control algorithms and the log, and may receive tip device profiles and boundary parameters from another device through a first interface (not shown). The log and other output data may be sent from the device 600 to other devices through a second interface (not shown) that may or may not be the same as the first interface. The base unit 608 may have a graphical display 610 and an operator interface 612 for interacting with the graphical display 610 and delivering operator input indications to the microprocessor. The embodiment 600 may be in connection with an operating characteristic controller (not shown), and operable to instruct the operating characteristic controller to adjust an operating characteristic source to a determined level.

Figure 7:
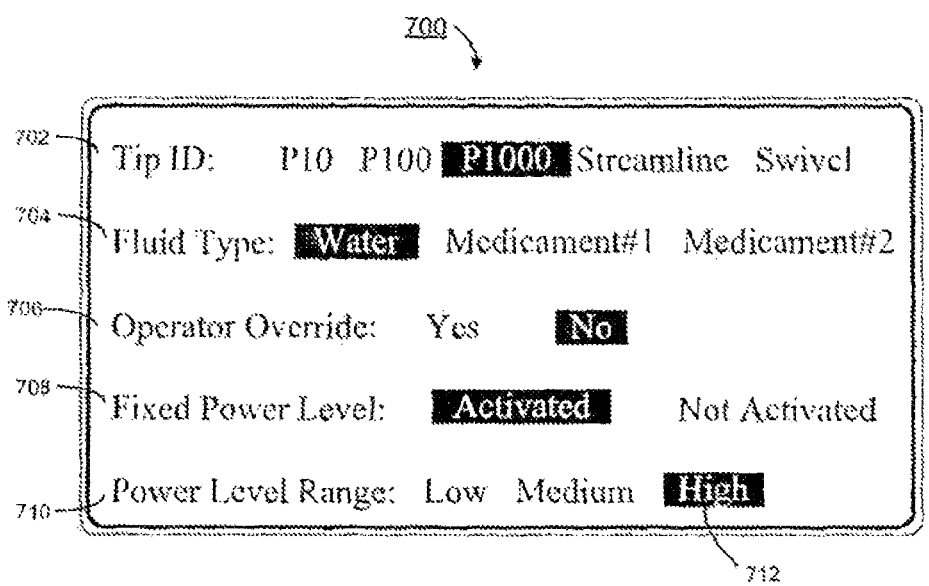
FIG. 7 illustrates an embodiment of a graphical display on the device in FIG. 6.

FIG. 7 illustrates an embodiment 700 of the graphical display 610 on the device 600 from FIG. 6. The embodiment 700 illustrates selectable conditions such as tip identification 702, fluid type 704, an indication if operator override is desired 706, fixed power level control 708 and power level range 710. The tip style 702 choices may be indicated by model number or characteristic. The power level range 710 may correspond to desired maximum and minimum operating boundary parameters. This set of conditions 702 704 706 708 and 710 are illustrative; other conditions may also be displayed by embodiment 700. The operator may use an input, such as reference 612 from FIG. 6, a mouse and cursor, a touch screen, buttons or other type of operator input mechanism to indicate desired options, as shown by reference 712. Other embodiments of a graphical display 610 such as drop-down menus, web-based interfaces, etc. may also possible.

Although the forgoing text sets forth a detailed description of numerous different embodiments, it should be understood that the scope of the patent is defined by the words of the claims set forth at the end of this patent. The detailed description is to be construed as exemplary only and does not describe every possible embodiment because describing every possible embodiment would be impractical, if not impossible. Numerous alternative embodiments could be implemented, using either current technology or technology developed after the filing date of this patent, which would still fall within the scope of the claims.

Thus, many modifications and variations may be made in the techniques and structures described and illustrated herein without departing from the spirit and scope of the present claims. Accordingly, it should be understood that the methods and apparatus described herein are illustrative only and are not limiting upon the scope of the claims.

What is claimed is:

1. A tip-based computer controlled system for a dental delivery device comprising:
    a dental delivery device in connection with an operating characteristic source, the dental delivery device comprising a handpiece, a tip and a non-volatile memory in the tip;
    an operating characteristic controller to control a value of an operating characteristic delivered to the dental delivery device from the operating characteristic source; and
    a data log maintained in the non-volatile memory, the data log comprising one or more events associated with a time period of the use of the tip.

2. The tip-based computer controlled system of claim 1, wherein the tip is enabled to receive data from the operating characteristic controller to store in the non-volatile memory.

3. The tip-based computer controlled system of claim 1, further comprising:
    an operator operating characteristic control input mechanism enabled to control the value of the operating characteristic delivered to the dental delivery device from the operating characteristic source.

4. The tip-based computer controlled system of claim 3, further comprising:
    a microprocessor in connection with the operating characteristic controller comprising an operating characteristic control algorithm corresponding to at least one of a group of detected conditions, the group comprising:
    a tip device profile corresponding to the tip, a proximity to one or more operating boundary parameters, a power level, a dental site temperature, a dental delivery device temperature, a dental hygiene material, a fluid type contained in a fluid supply, a safety feedback loop, and an error circumstance;
    wherein during a period of use of the tip for a dental procedure, the operating characteristic control algorithm automatically determines a desired value of the operating characteristic delivered to the dental delivery device based on the tip and the at least one of the group of detected conditions, and automatically adjusts a current value of the operating characteristic to the desired value via the operating characteristic controller so that the dental device operates in conjunction with the desired value of the operating characteristic during at least a portion of the period of use of the tip.

5. The tip-based computer controlled system of claim 4, wherein the tip is enabled to receive data from the microprocessor to store in the non-volatile memory.

* * * * *